United States Patent [19]

Rose et al.

[11] Patent Number: 4,695,954
[45] Date of Patent: Sep. 22, 1987

[54] MODULAR MEDICATION DISPENSING SYSTEM AND APPARATUS UTILIZING PORTABLE MEMORY DEVICE

[76] Inventors: Robert J. Rose, 201 East First, Park Rapids, Minn. 56470; Russell L. Trimble, 70 Carriage Lane, Burnsville, Minn. 55337

[21] Appl. No.: 663,916

[22] Filed: Oct. 31, 1984

[51] Int. Cl.$^4$ ............................................. G06F 15/42
[52] U.S. Cl. .................................. 364/413; 364/415; 364/479; 221/2; 221/3; 221/9; 221/15
[58] Field of Search ............... 364/400, 413, 415, 479; 340/309.2, 309.3, 309.4, 309.15; 221/2–3, 7–9, 15; 206/528, 534, 534.1, 534.2, 538–540, 533

[56] References Cited

U.S. PATENT DOCUMENTS

| | | | |
|---|---|---|---|
| 2,853,182 | 9/1958 | Barnett | 206/38 |
| 2,948,106 | 8/1960 | Blumstein | 58/57.5 |
| 3,395,829 | 8/1968 | Cogdell et al. | 221/15 |
| 3,474,617 | 10/1969 | Robinson et al. | 58/16.5 |
| 3,739,740 | 6/1973 | Fromer | 116/121 |
| 3,762,601 | 10/1973 | McLaughlin | 221/2 |
| 3,911,856 | 10/1975 | Ewing | 116/121 |
| 3,998,356 | 12/1976 | Christensen | 221/2 |
| 4,034,757 | 7/1977 | Glover | 128/260 |
| 4,084,415 | 4/1978 | Corman | 70/269 |
| 4,223,801 | 9/1980 | Carlson | 221/3 |
| 4,258,354 | 3/1981 | Carmon et al. | 340/309 |
| 4,275,384 | 6/1981 | Hicks et al. | 340/309 |
| 4,290,114 | 9/1981 | Sinay | 364/415 X |
| 4,293,845 | 10/1981 | Villa-Real | 340/309 |
| 4,360,125 | 11/1982 | Martindale et al. | 221/2 |
| 4,361,408 | 11/1982 | Wirtschafter | 368/10 |
| 4,382,688 | 5/1983 | Machamer | 368/10 |
| 4,448,541 | 5/1984 | Wirtschafter | 368/10 |
| 4,473,884 | 9/1984 | Behl | 364/479 |
| 4,572,403 | 2/1986 | Benaroya | 221/3 |
| 4,616,316 | 10/1986 | Hanpeter et al. | 364/413 |

*Primary Examiner*—Gary V. Harkcom
*Attorney, Agent, or Firm*—Kinney & Lange

[57] ABSTRACT

A system, apparatus and method for dispensing medications prescribed by a doctor or other medical personnel. A portable memory device (such as a magnetic card) is used to store data representing prescription information. Prescription information is encoded into the memory device by a programming device located in a pharmacy. A container having a plurality of individual compartments is filled at the pharmacy with medications in accordance with the prescription information. The portable memory device and filled container are transported together to a medication dispenser located near a patient. The dispenser includes apparatus which reads the prescription information from the memory device and makes medications within the individual compartments available to the patient only at prescribed times. The medication dispenser also includes apparatus for monitoring whether or not the patient is complying with the prescribed medication schedule. Patient compliance information is stored within the memory device. The system also includes a monitor through which medical personnel can obtain a video display or printed record of the prescription information and patient compliance information stored within the memory device.

45 Claims, 10 Drawing Figures

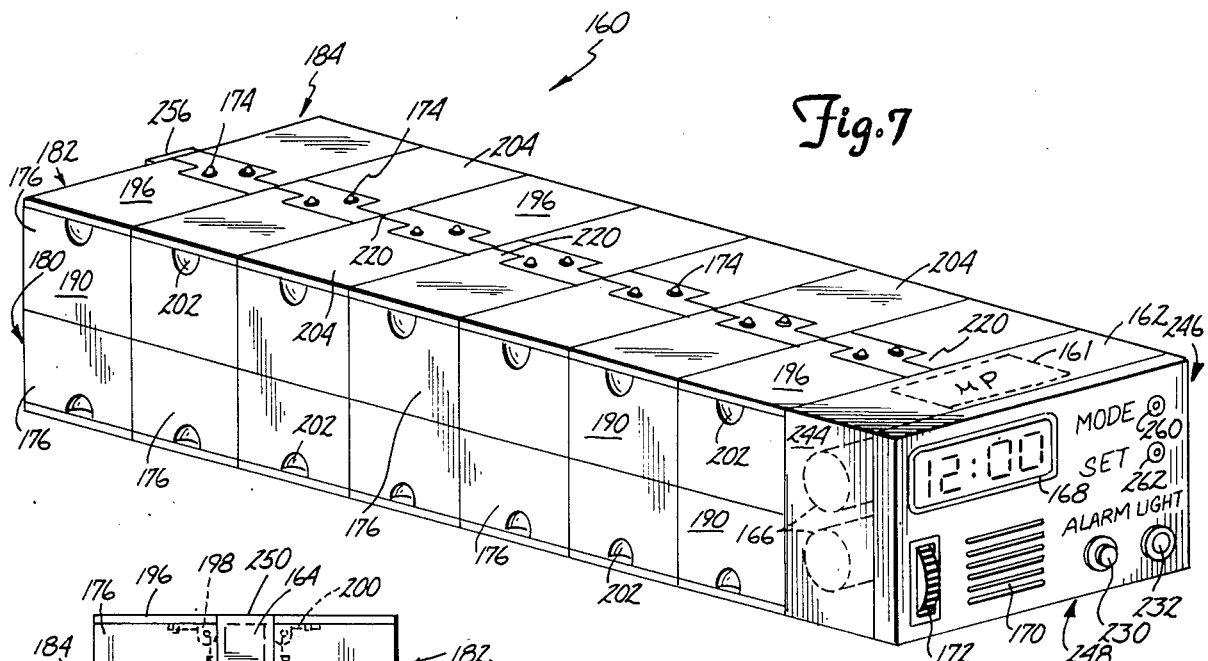
Fig.7
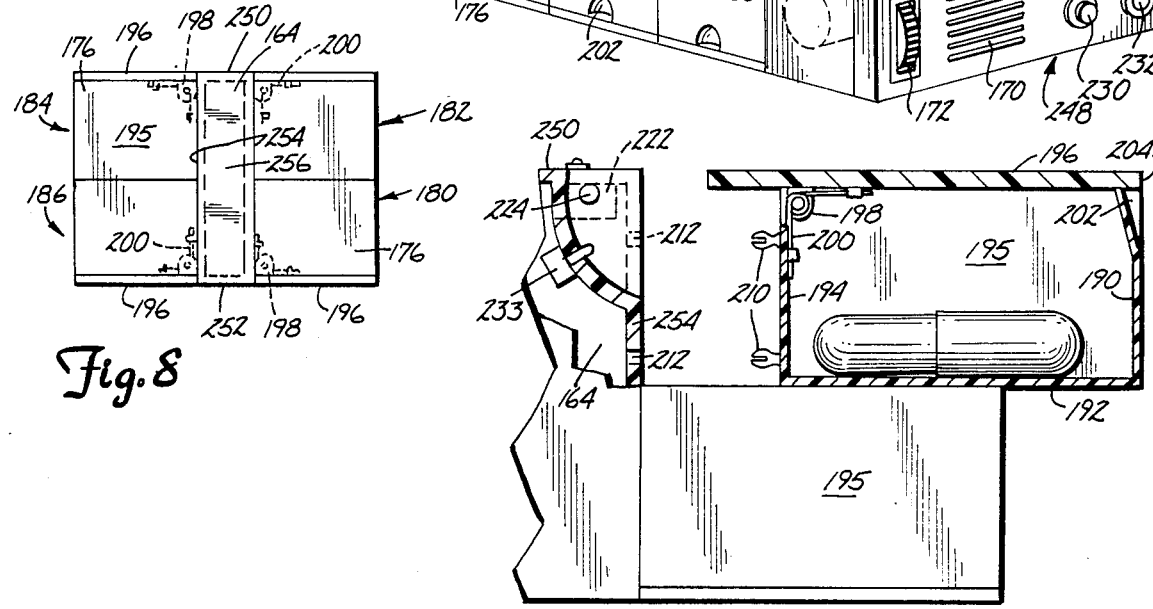
Fig.8
Fig.9
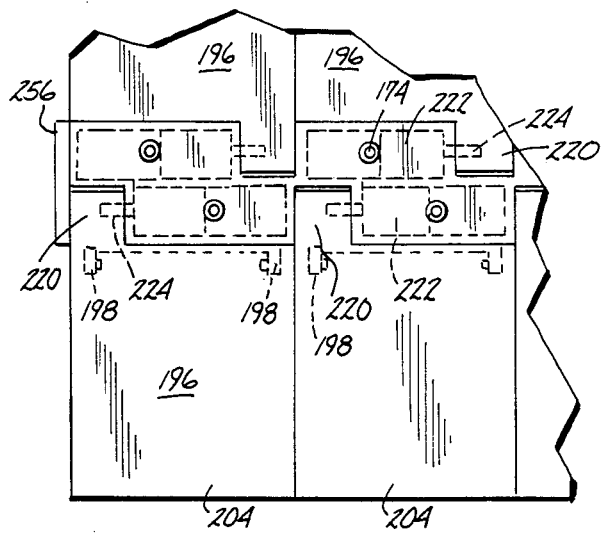
Fig.10

MODULAR MEDICATION DISPENSING SYSTEM AND APPARATUS UTILIZING PORTABLE MEMORY DEVICE

BACKGROUND OF THE INVENTION

1. Field of the Invention

The present invention relates to medication dispensers. In particular, the present invention is a system, apparatus and method for distributing medications, and for dispensing the medications to a patient at prescribed times.

2. Description of the Prior Art

Medical studies have repeatedly shown that poor patient compliance with a prescribed medication schedule is a major problem in the treatment of chronic diseases. It has been estimated that up to 50% of all Americans taking chronic medications do so inaccurately. Noncompliance results in high rates of illness, hospitalization and even death. All demographic, social, personality and disease groups are susceptible to this problem.

Of all the reasons for noncompliance, forgetfulness is the most common. A patient will typically try to remember times at which medications are to be taken. This mental calculation technique often works poorly. Even if the correct times are remembered, they are often missed. Poor vision has been identified as another significant factor leading to noncompliance. Patients who are unable to read the labels affixed to medication containers find it extremely difficult to follow a medication program. Physical impairments, such as arthritis, which make it difficult for patients to open medication containers, are yet another factor contributing to noncompliance.

Although the factors identified above affect people of all ages, noncompliance is particularly prevalent among the elderly. As more members of our population achieve older ages, debilitating physical impairments and chronic mental disorders are becoming increasingly common. These elderly people are often on a rigorous medication program. Despite these problems, many elderly people strive to live independently outside of institutions. One of the primary factors in determining whether or not they can remain in their own home, in fact, depends on their ability to regularly and accurately self-medicate.

The prior art is replete with portable medication dispensers which include timing and alarm devices. Generally, these devices are simply comprised of an alarm which is attached to a pill box. U.S. Pat. Nos. 4,448,541, 4,382,688, 4,361,408, 4,275,384, 4,258,354, 4,223,801 and 3,474,617 are examples. Although useful, these devices have their drawbacks. Those which are used to dispense more than one type of medication, such as U.S. Pat. No. 4,258,354, require a coded display. The patient must then match the alarm code to the type of medication which is to be taken. This procedure is confusing.

None of the devices identified above is suitable for use with the large scale medication distribution systems used within hospitals and nursing homes. Under current practice within these institutions, pharmacists fill prescriptions for each individual patient in advance of the time at which they are to be administered. The medications are then delivered to the nursing unit area by other personnel. Nurses then distribute medications to each patient at the prescribed times. This system is extremely expensive and time consuming. Furthermore, since medications are being distributed to a large number of patients, the error rate is relatively high.

Devices which attempt to alleviate the burden of distributing medications within hospitals and nursing homes are also disclosed in the prior art. U.S. Pat. No. 3,762,601 is one such device. A cabinet contains a plurality of compartments, each having an individual time lock and alarm. Each compartment contains medications which a patient is to receive at a prescribed time. The cabinet is positioned near a patient's bed and the individual time locks are programmed to open at the prescribed times throughout a 24-hour period. The utility of this device is limited. A pharmacist, doctor or other authorized person is still required to transport medications to the container and fill the individual compartments in accordance with the prescription. When signaled by an alarm, a nurse must enter the patient's room, unlock the main door and remove the medication from the particular compartment before administering it to the patient. There is little savings in either time or expense.

U.S. Pat. No. 4,293,845 discloses a multi-patient medication programmer and alarm system. Although this device may simplify medication scheduling, it does nothing to alleviate the burden of distribution. Each time an alarm goes off, a nurse must administer medications to the patient.

U.S. Pat. No. 3,998,356 is an electronically-controlled device for dispensing medications. Medications are stored within magazines, each of which contains a plurality of rotatable compartments. At the preprogrammed times the dispenser is activated to rotate the proper magazine and dispense the required medications. This device is relatively complicated, in both electronic and mechanical aspects. It is not well suited for individual patient use.

It is apparent that hospitals and nursing homes are using archaic, inefficient and expensive systems to distribute medications to their patients. At the same time, nearly one-third of all hospital and nursing home patients are responsible enough to take their own medications if they are presented to them at the appropriate times. What is needed, therefore, is an automated medication distribution system which will enhance the reliability of patient self-medication. The system should be less labor-intensive and less expensive than those currently in use. Furthermore, the system should accommodate the increasingly important role of pharmacists in supervising patient medication programs. The medication distribution system should include dispensers which can be programmed to distribute proper medications to patients at prescribed times. The dispenser should be capable of being quickly filled with all medications a patient will need. A dispenser which will operate over a period of 24-hours, or longer, is desirable. The medications should be packaged for convenient distribution to the patient.

SUMMARY OF THE INVENTION

The present invention is a system, apparatus, and method for distributing and dispensing medications to patients. The system is especially well suited for hospital and nursing home use where some patients are capable of administering medications to themselves. Outpatient applications are also accomodated. The system greatly increases the efficiency and reduces the costs of large scale medication distribution.

Included are memory means for storing data. Programming means are used to store data representing prescription information within the memory means. The system also includes dispenser means for dispensing medications to a patient. The dispenser means includes both means for reading the data from the memory means, and means for making the prescribed medications available to the patient in accordance with the prescription information.

Preferred embodiments of the medication dispensing system also include monitor means for displaying the prescription information which is stored within the memory means. The monitor means is either a printer or a video display. The system also includes transmitter means for transmitting over a communication line the data stored within the memory means.

A preferred embodiment of the medication dispensing device includes container means having a plurality of individual compartments. Each compartment is filled, in accordance with the prescription information, with medications which are to be taken at a prescribed time. The container means is then positioned on a control module. The control module includes both means for reading the data representing prescription information from the memory means and means for making each individual compartment and the medications therein accessible to the patient only at the prescribed time.

Sensor means monitor patient compliance with the prescription information. Means for storing patient compliance information within the memory means is also included. A printer within the control module can produce a printed record of the compliance information. Other embodiments include transmitter means for transmitting compliance information to the monitor.

BRIEF DESCRIPTION OF THE DRAWINGS

FIG. 4 is a sectional view of the containers taken along lines 5—5 of FIG. 3.

FIG. 7 is a perspective view of a medication dispensing device for home use.

FIG. 8 is a rear view of the home unit.

FIG. 9 is a detailed rear view of the home unit with parts thereof shown in sectional form.

FIG. 10 is detailed top view of the home unit.

DETAILED DESCRIPTION OF THE PREFERRED EMBODIMENTS

A. SYSTEM AND METHOD OF USE

Figure 1:
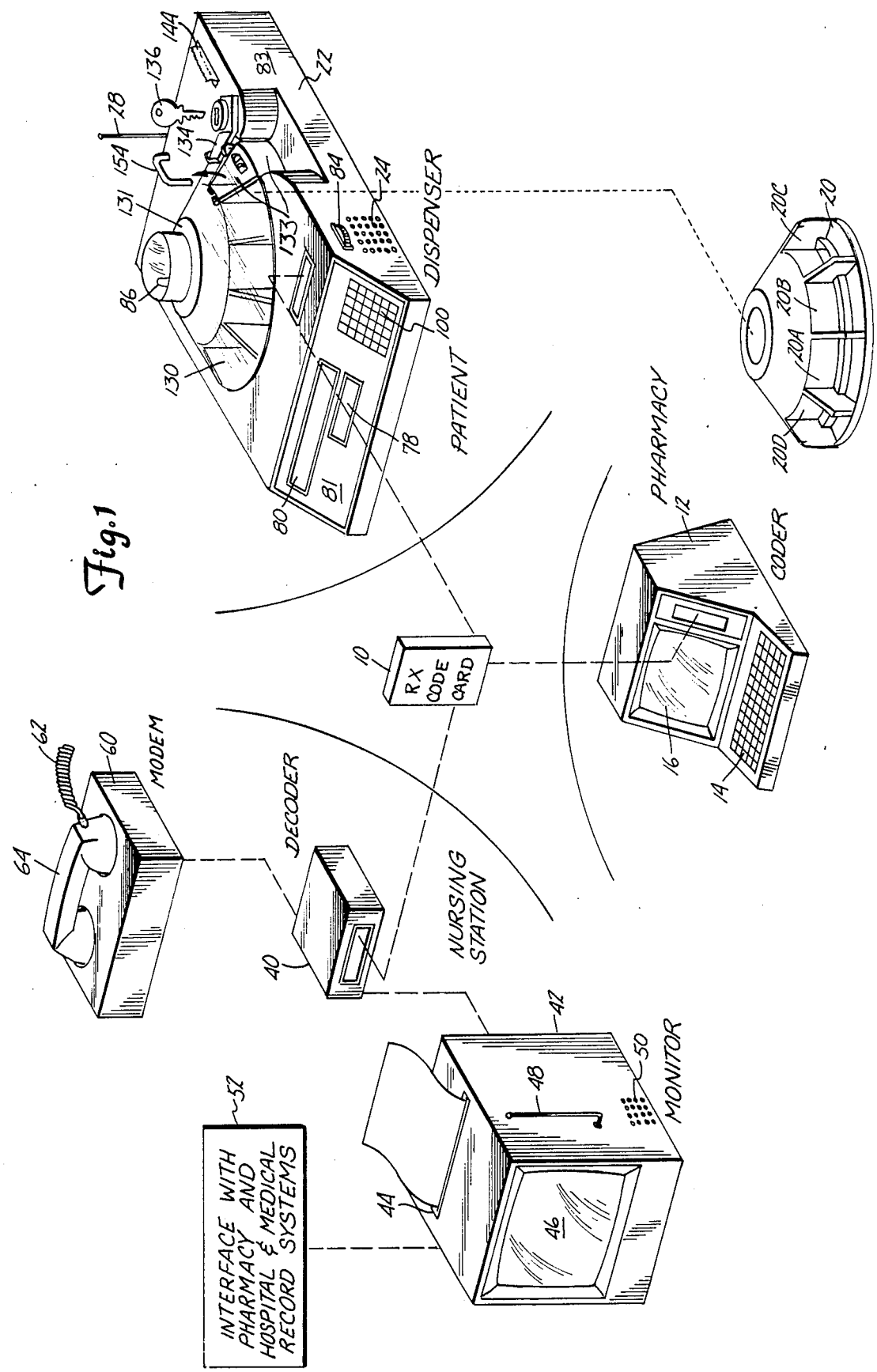
FIG. 1 illustrates the elements of the medication dispensing system of the present invention.

Components of the medication dispensing system of the present invention are illustrated diagrammatically in FIG. 1. The system is very versatile and is well suited for home, hospital and nursing home use. The system is particularly well suited for use in hospitals and nursing homes where a large number of patients must receive medications on regular schedules. In addition to dispensing medications on a regular schedule, the system can accommodate "stat" or immediate changes in a patient's medication program. The medication dispensing system of the present invention greatly simplifies the logistical problems encountered by these institutions. The time and expense required to dispense medications and record patient compliance with the medication schedule are also reduced.

As shown in FIG. 1, the medication dispensing system includes apparatus which are located in a pharmacy, at a nursing station, and with the patient. Rx code card 10 is a central element of the medication dispensing system and is used in conjunction with all other devices. Code card 10 is a nonvolatile memory device capable of having data written to or stored within it. Data stored within code card 10 can also be read or retrieved therefrom. In preferred embodiments, code card 10 is comprised of magnetic memory such as commercially-available floppy diskettes. Other types of nonvolatile memory including integrated circuit memory are equally well suited. A label or other type of graphic representation (not shown) will typically be positioned on code card 10 to identify the patient and/or institution.

Rx code card 10 is used to store data representing a wide variety of information. Throughout the remainder of the specification, all data stored within code card 10 which is utilized to operate the various devices of the system will be characterized as "prescription information." Prescription information includes all data which may be of use to hospital personnel, doctors, pharmacists, or the patient.

Patient identification data, such as name, address, file or identification number, insurance or other patient information utilized by hospital or nursing home personnel, is included for recordkeeping purposes. Of particular utility to the system of the present invention is medication data. Medication data stored within code card 10 includes a complete description of the patient's medication program. This description includes a list of all medications which the patient is currently receiving, dosages of each, and a schedule identifying the times at which the medications are to be taken. Data representing prescription information is preferably entered within code card 10 in a predetermined format. This facilitates standardization within the system.

Located within the pharmacy is a programming device such as coder 12. Using a coder 12, a pharmacist or other authorized personnel will program all prescription information regarding an individual patient onto code card 10. As shown in FIG. 1, coder 12 receives Rx code card 10. All prescription information to be encoded onto code card 10 is entered into coder 12 in alphanumeric form through keyboard 14. Preferred embodiments of coder 12 include video display 16 through which the operator is able to observe information being written to code card 10. In this way accuracy of the prescription information can be ensured.

Data entered into coder 12 through keyboard 14 is processed by electronic circuitry (not shown) into a form capable of being encoded onto code card 10. In preferred embodiments, prescription information is encoded onto code card 10 in digital form. In those embodiments in which code card 10 comprises magnetic memory, a transducer (not shown) such as a magnetic read/write head or a disk drive, is used to enter the data within code card 10. In other embodiments in which code card 10 is comprised of integrated circuit memory, digital data can be entered directly into the code card.

At the pharmacy a pharmacist or other authorized personnel will fill a container, illustrated generally at 20, with medications in accordance with the prescription information stored within code card 10. For purposes of example, the embodiment shown in FIG. 1 includes four individual compartments, 20A, 20B, 20C and 20D. Unlike conventional medication distribution systems in which the medications are positioned in compartments according to the type of medication, in the present invention a pharmacist will fill the individual compartments with medications in accordance with the time at which they have been prescribed to be taken. For example, compartment 20A will contain all medications which a patient is to take immediately upon waking in the morning, say 8:00 A.M. This will likely include several medications since the patient has been sleeping for the past several hours. At 10:00 A.M. the patient may be required to take another dose of medication. This medication will be located within compartment 20B. Similarly, at 12:00 P.M. the patient may be required to take several medications prior to eating lunch. Once again, all these medications will be located within the same compartment, say 20C.

After Rx code card 10 has been programmed with all prescription information, and container 20 has been filled in accordance therewith, both will be transported together to the patient location and inserted within medication dispenser 22. In hospitals and nursing homes, medication dispenser 22 will typically be positioned at the bedside of a patient or on an IV support pole. For home use, dispenser 22 is best positioned at a location such as a medicine cabinet which is safely out of reach of young children.

Medication dispenser 22 reads the data representing prescription information from code card 10. Dispenser 22 also makes medications within the individual compartments of container 20 available to the patient at the prescribed times in accordance with the prescription information. To prevent problems inherent with dispensers of the prior art, dispenser 22 prohibits access to the medications at times other than those programmed within code card 10.

At the prescribed times, medication dispenser 22 will generate alarms indicating to the patient that it is time for him to take his medications. The preferred embodiments include both an audio alarm such as a beeping tone produced by speaker 24 and a visual alarm produced by light 86.

It is highly desirable for patients take medications only at the prescribed times. Information regarding patient compliance with the prescribed medication schedule is required by hospital and nursing home staff in order to make informed decisions regarding a patient's care program. Medication dispenser 22 therefore includes apparatus for sensing whether the patient is taking the medications when they are made available and thereby complying with the medication program. Patient compliance information can be transmitted to the nursing station through a transmitter and antenna 28. Alternatively, patient compliance information can be recorded on paper by printer 144. These and other functions of dispenser 22, as well as the apparatus and mechanical systems for implementing them, will be described in detail in later sections of this specification.

Prescription information and patient compliance information stored with Rx code card 10 includes a complete medical record or history of a patient. Doctors and other hospital or nursing home personnel regularly require access to this information. The system of the present invention therefore includes decoder 40 and monitor 42 for producing a record of all information stored within code card 10. Decoder 40 and monitor 42 are typically located at a nursing station or other information retrieval center where personnel require access to this information.

Decoder 40 is a device which receives code card 10 and generates electrical signals representing all information stored therein. In preferred embodiments, decoder 40 includes a transducer such as a magnetic read/write head or disk drive for reading data from code card 10 comprised of magnetic memory. Electronic circuitry for converting this information into a stream of digital data is also included. In other embodiments in which code card 10 is comprised of an integrated circuit memory device, decoder 40 includes electronic circuitry for reading prescription information stored within code card 10 and converting that information into a digital data stream.

Monitor 42 is connected to receive the data stream generated by decoder 40. Preferred embodiments of monitor 42 include a printer 44 for producing a printed record of the prescription information and a video display 46 for producing a video representation of the prescription information. Video display 46 is particularly useful when it is desired to quickly view specific items of information. Monitor 42 also preferably includes an antenna 48 and radio receiver (not shown) for receiving prescription information and patient compliance information directly from medication dispenser 22. A speaker 50 is also included to alert nursing personnel of patient noncompliance in critical circumstances. Monitor 42 is also capable of being interfaced directly with a computerized record-keeping system 52 of the hospital, pharmacy, or nursing home.

It is becoming increasingly common to transmit medical information regarding a particular patient over communication lines. Typically, this information is transmitted through a conventional telephone network. Systems for transmitting vital sign information in this way are well developed. The medication dispensing system of the present invention includes modem 60 for transmitting prescription information and patient compliance information.

As shown in FIG. 1, modem 60 is connected to receive the data representing prescription information generated by decoder 40. Modem 60 includes electronic circuitry for converting this data into a format which can be modulated onto and transmitted through a communication line 62, such as a standard telephone network. In preferred embodiments, modem 60 will modulate the data into tones or pulses which can be entered into communication line 62 directly through a standard telephone handset 64.

B. HOSPITAL MEDICATION DISPENSER

Figure 2:
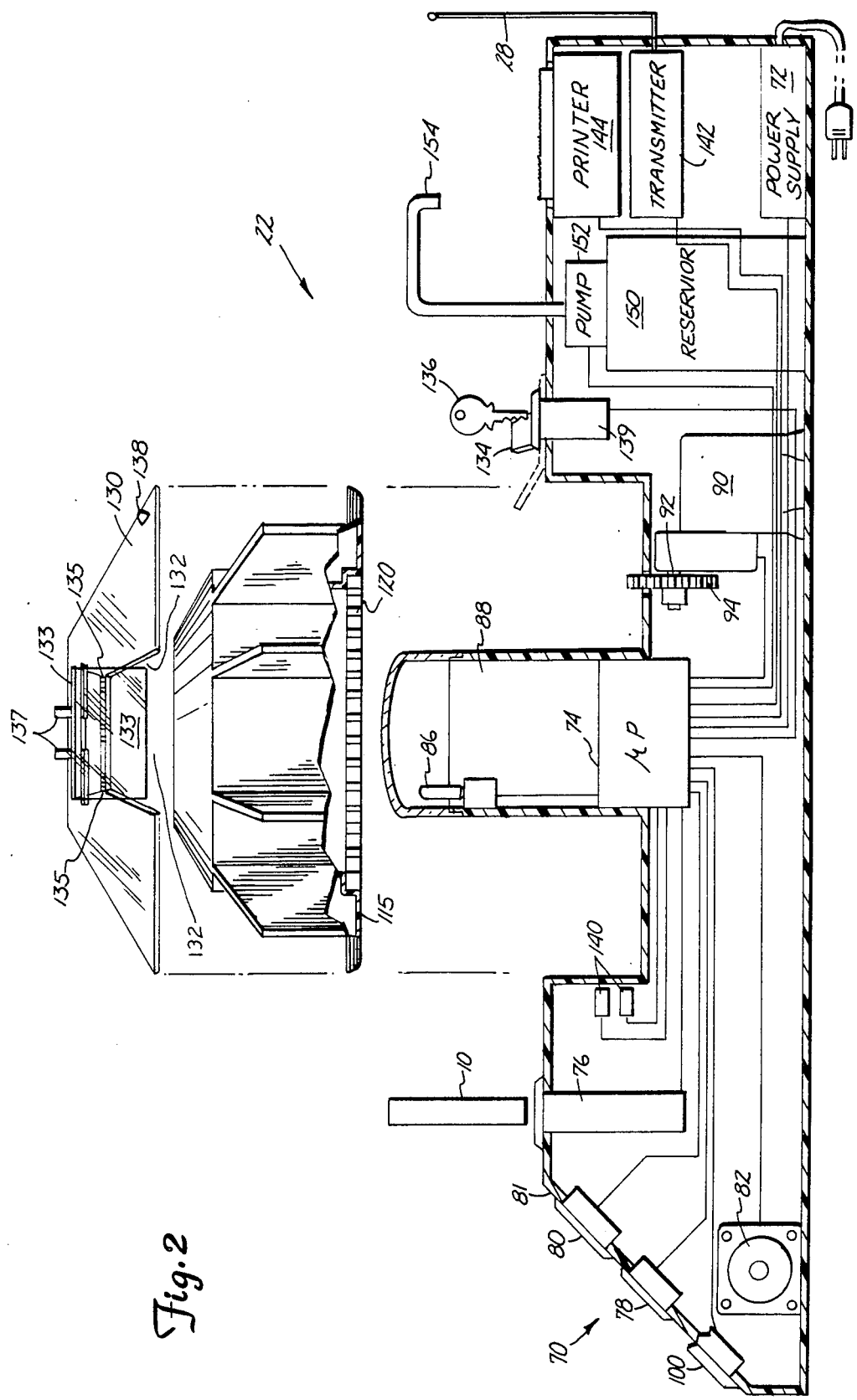
FIG. 2 is an exploded side view of the medication dispenser for hospital and nursing home use with parts thereof shown in sectional form.

A preferred embodiment of medication dispenser 22 is illustrated in FIGS. 2-6. This embodiment is well suited for use in hospitals, nursing homes and other institutions in which medications must be distributed to a large number of patients. As shown in FIG. 2, medication dispenser 22 includes a control module 70. All electrical and mechanical systems of medication dispenser 22 are conveniently packaged within control module 70. Power supply 72 provides electrical energy for all electrical and electronic systems within control module 70. In preferred embodiments, power supply 72 is powered by a standard 120 volt AC electrical outlet. Other embodiments include rechargeable batteries. Although the interconnections are not shown in FIG. 2, power supply 72 provides electric current to all electrical and electronic devices contained within control module 70.

The central element of medication dispenser 22 is a control device such as microprocessor 74. Microprocessor 74 coordinates and controls all functions of control module 70. Although not shown, microprocessor 74 will include Input/Output ports, random access memory (RAM), read only memory (ROM), and a real time clock.

As shown in FIG. 2, microprocessor 74 is interfaced to transducer 76. Transducer 76 is a device which, under control microprocessor 74, reads data from and writes data to Rx code card 10. In preferred embodiments, transducer 74 is a magnetic read/write head for reading data from and writing data to a magnetic memory device. In other embodiments, transducer 76 comprises an electrical socket into which an integrated circuit memory device is plugged. In still other embodiments, transducer 76 includes an optical sensor.

Medication dispenser 22 includes clock display 78 and message display 80, both of which are mounted to a front face 81 of control module 70. In preferred embodiments both clock display 78 and message display 80 are digital displays driven by microprocessor 74 and are, for example, commercially available LED or LCD displays. Clock display 78 displays the correct time of day. Microprocessor 74 causes various messages stored within ROM to be displayed on message display 80 in response to predetermined input parameters. The message TIME TO TAKE PILLS is, for example, displayed on message display 80 each time dispenser 22 presents medications to the patient.

Medication dispensing device 22 produces both audio and visual alarms to alert the patient at times medications are to be taken. An audio transducer such as speaker 82 is mounted to a side panel 83 of control module 70 and is interfaced with microprocessor 74. At the prescribed times, microprocessor 74 causes speaker 82 to generate an audio alarm, such as a beeping tone. The volume of the alarm generated by speaker 82 can be varied by volume control 84, shown in FIG. 1. A visual alarm, such as light 86, is positioned within a central post 88 of control module 70. Light 86 is interfaced with, and controlled by, microprocessor 74 so that it is lit (either continuously or in a flashing manner) at the prescribed times, thereby providing the patient with a visual indication that medications are to be taken. This alarm is particularly useful for older patients who are often hard of hearing and thereby unable to hear the audio alarm generated by speaker 82.

An actuator such as stepper motor 90 is used to rotate container 20 which is positioned onto control module 70. As shown in FIG. 2, stepper motor 90 includes a shaft 92 which has a gear 94 mounted thereon. Stepper motor 90 is interfaced with microprocessor 74 and is actuated by control signals received from microprocessor 74.

Hospital and nursing home personnel must often make immediate changes to a patient's medication program. These changes must be made after container 20 has already been prefilled with medications by the pharmacist, and code card 10 programmed in accordance therewith. Medication dispensing device 22 includes a keyboard 100 for accommodating these immediate orders. As shown in FIG. 2, keyboard 100 is mounted to a front face of control module 70 and is interfaced with microprocessor 74. Utilizing keyboard 100, hospital or nursing home personnel can make immediate changes to the presription information stored within Rx code card 10. Compartments within container 20, of course, will then be refilled accordingly by the medical personnel.

Figure 3:
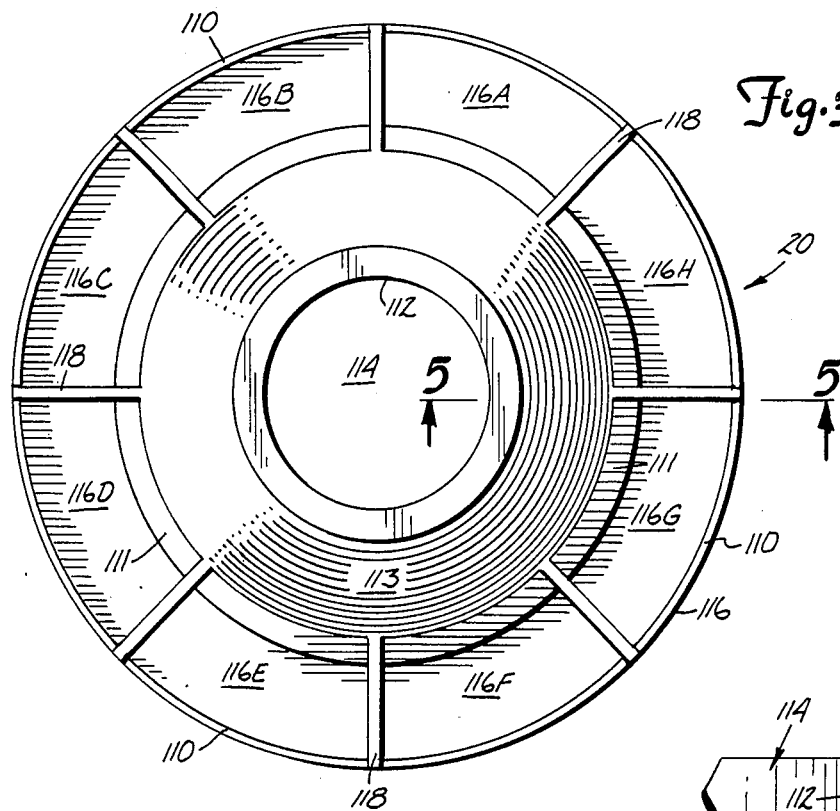
FIG. 3 is a top view of a container used with the hospital unit.
Figure 5:
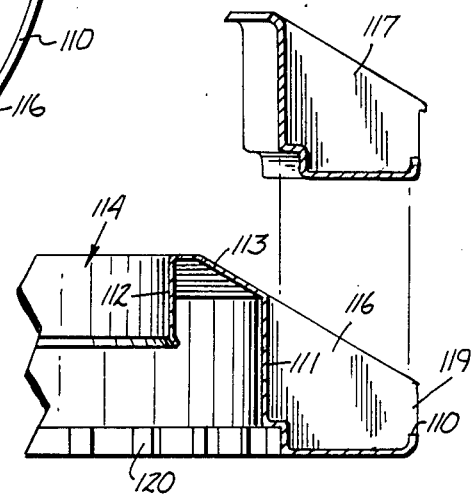

Preferred embodiments of container 20 are illustrated in FIGS. 3-6. As best shown in FIG. 3, container 20 is toroidal in shape and has a generally vertical outer lip 110, a generally vertical intermediate wall 111, a generally vertical inner wall 112, a sloped top surface 113, a center opening 114, and a bottom 115. Container 20 includes a plurality of individual compartments 116 circumferentially arranged about its periphery. The embodiment shown in FIG. 3 includes eight individual compartments, 116A–116H. The number of compartments 116 included within container 20 can vary depending upon system requirements such as the number of medications a patient is expected to take, and the length of time for which it is desired to use container 20 without refilling. Individual compartments are separated from adjacent compartments by generally vertical radial walls 118. Each compartment 116A–116H is sized large enough to hold one or more medications. Compartments 116A–116H can also be sized to hold small containers of liquid medication. As best shown in FIGS. 2 and 5, compartments 116A–116H include open side 119 between sloped top surface 113 and lip 110 to permit access to the medications contained therein.

Figure 4:
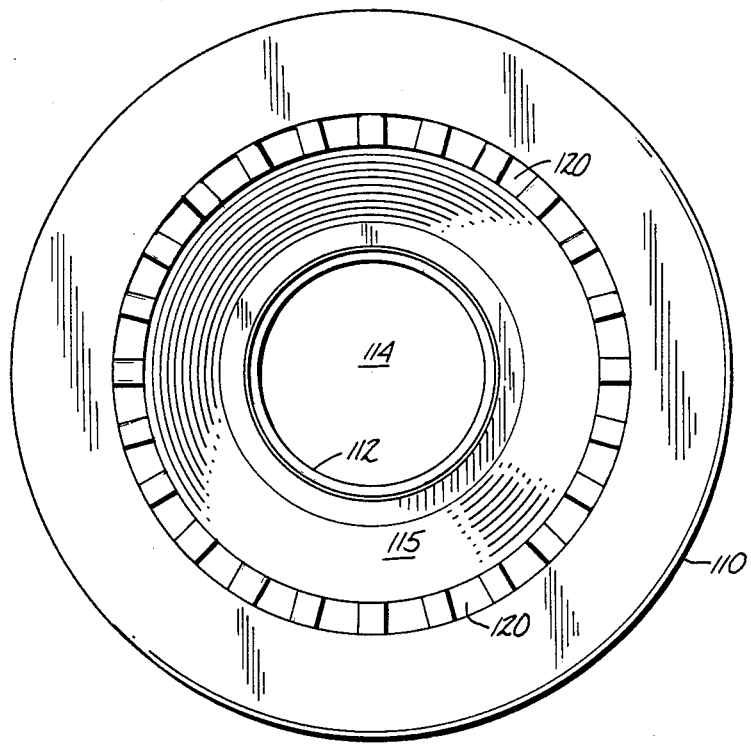
FIG. 4 is a bottom view of the container used with the hospital unit.

As shown in FIG. 4, a plurality of gear teeth 120 are circumferentially arranged about a bottom 115 of container 20. Gear teeth 20 will engage gear 94 when container 20 is positioned onto control module 70. When actuated, stepper motor 90 transmits rotational motion to container 20 through gear 94 and gear teeth 120.

Containers 20 are preferably made of lightweight and inexpensive material, such as plastic. Containers 20 can then be disposed of after each use. Alternatively, if it is desired to reuse containers 20, an inexpensive liner 117 manufactured of paper or plastic can be inserted within the compartments 116A–116H.

Figure 6:
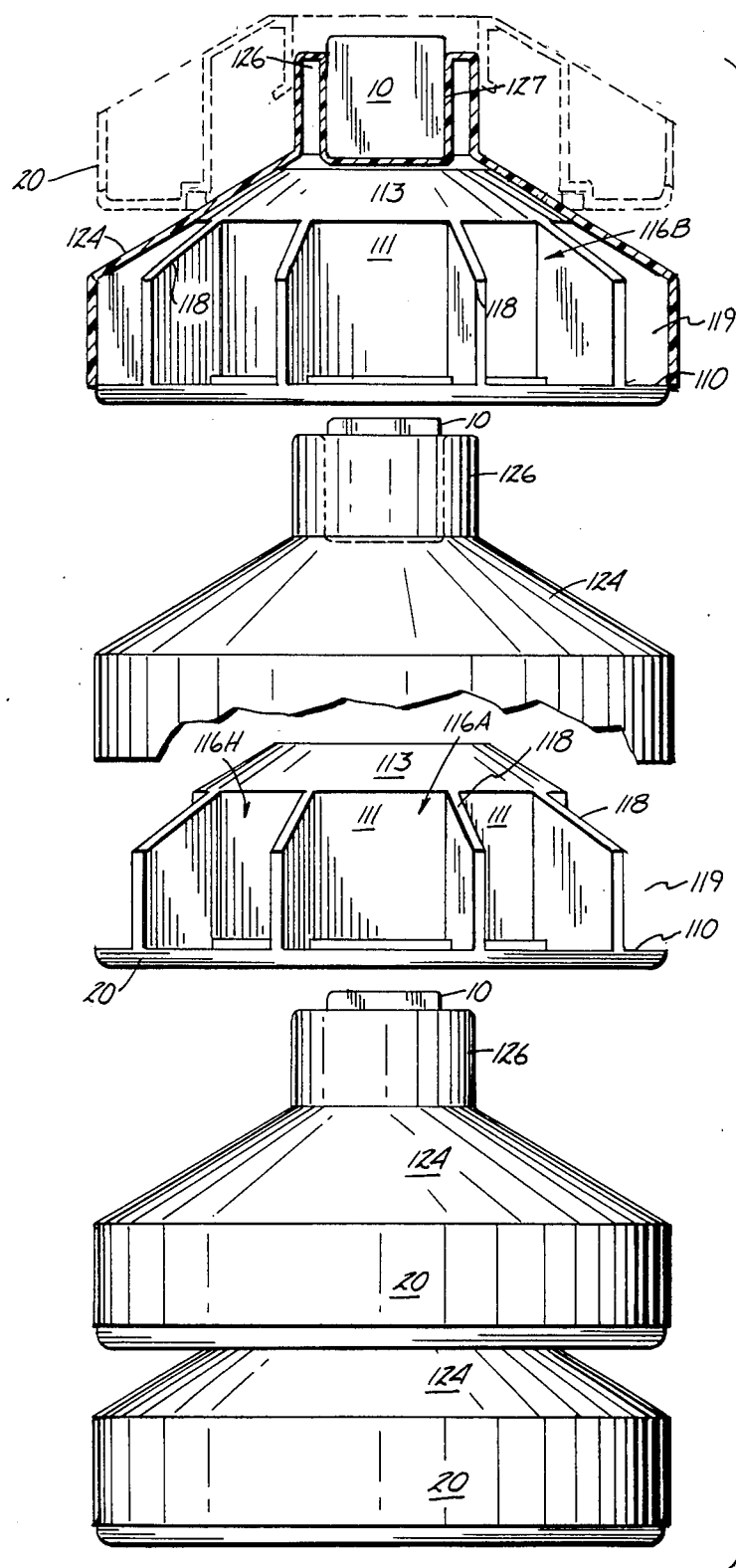
FIG. 6 is an exploded view showing the containers stacked for transportation.

As illustrated in FIG. 6, containers 20 are designed in such a way that they can be easily stacked and transported between various locations. After each container 20 has been filled with medications at the pharmacy, a cap 124 is positioned over top surface 113 of container 20. Cap 124 has a diameter sufficient to cover the openings of compartments 116–116H and prevent the medications therein from being spilled in the event that container 20 is accidentally tipped on its side. As shown, each cap 124 includes an upper extension 126 which has a diameter slightly less than the diameter of central opening 114 within container 20 to allow extension 126 of cap 124 to fit within central opening 114 of container 20. In this way a plurality of containers 20 can be stacked on top of one another and conveniently transported from the pharmacy to the individual patient rooms.

To keep the proper code card 10 associated with its respective container 20, each cap 124 includes means for conveying the code card 10 along with the respective container. As shown in FIG. 6, code card 10 can be inserted within a receptacle opening 127 in extension 126. Alternatively, each cap 124 may include a clip on its side into which the respective code card 10 is fastened. Using this system, hospital or nursing home personnel who transport medications to the individual patients will know the proper code card 10 to be associated with each container 20. In preferred embodiments, each container 20 will also include an identification number which corresponds to a similar number located on the respective code card 10. In the event that a code card 10 is misplaced from its respective container 20 these numbers provide a means of identification by which the two can be reassociated.

The operation of medication dispensing device 22 is best illustrated in FIGS. 1 and 2. After being filled with medications and transported to the proper patient, container 20 is positioned onto control module 70 with central post 88 extending through central opening 114 of container 20. Container 20 is thereby free to rotate about central post 88 when driven by stepper motor 90. After container 20 has been placed onto control module 70, a cover 130 is positioned over a top side of the container. Like container 20, cover 130 is circular and has a central opening 131 which fits around central post 88 of control module 70. Cover 130 encloses the open sides 119 of all compartments 116A-116H of container 20.

Cover 130 includes an opening 132 which is equal in size to the open side 119 of one of the compartments 116A-116H. It is through opening 132 that a patient is able to access medications within the compartment 116A-116H which is aligned with the opening 132. Preferred embodiments of medication dispenser 22 include a door 133 which covers opening 132. In the embodiment shown in FIG. 2, door 133 is mounted to cover 130 by hinges 135. Other embodiments (not shown) include a sliding door 133 mounted to side panel 83. Door 133 also includes a spring biased safety latch 137. A patient must compress latch 137 while at the same time opening door 133. This two step procedure prevents unauthorized access by children. Other safety latches are equally well suited.

Control module 70 also includes lock 134 which is activated by key 136. After cover 130 is positioned over container 20, lock 134 is turned into position to lock the cover 130 onto control module 70. In this way only authorized persons having access to key 136 can remove container 20, or the medications therein, from control module 70. As shown, lock 134 engages lug 138 which is positioned on the top side of cover 130. Cover 130 is thereby engaged with control module 70. This mechanism prevents a patient from rotating opening 132 of cover 130 to compartments 116 at will.

Key 136 also actuates switch 139, which is interfaced with microprocessor 74. Switch 139 is used to initiate the operation of dispenser 22 after container 20, cover 130 and Rx code card 10 have been positioned into control module 70.

Once activated, microprocessor 74 causes stepper motor 90 to rotate container 20 and position the proper compartment 116A-116H in alignment with opening 132 at the prescribed times in accordance with the prescription information stored within code card 10. In this way, medication dispenser 22 makes the medications within compartments 116A-116H available to the patient only at the prescribed times. The patient simply opens door 133, reaches into opening 132, and removes the medications from the compartment 116A-116H which is presented. The patient then self-administers the medications. Each time container 20 is rotated to align one of compartments 116A-116H with opening 132, light 86 will be lit and speaker 82 will produce a beeping tone. These alarms indicate to the patient that medications are accessible.

At each prescribed time a new compartment (eg. 116B) is rotated in alignment with opening 132. At the same time, the adjacent compartment (eg. 116A) previously in alignment with opening 132 is rotated under cover 130. Medications within that compartment (116A) will, therefore, no longer be accessible to the patient if they were not taken at the prescribed time. Compliance information indicative of whether or not the patient has taken the prescribed medications is used by hospital and nursing home staff to make informed decisions regarding a patient's care program. Control module 70 includes sensors 140 for sensing patient compliance with the prescribed medication schedule. Sensors 140 detect the presence of medications within the compartment which has been rotated beyond opening 132 and therefore underneath cover 130. Sensors 140 are interfaced with microprocessor 74 and produce signals indicative of the presence or absence of medications. In preferred embodiments, sensors 140 are comprised of reflective photo-emitter/detector devices. Container 20 is a clear or translucent material to enable sensors 140 to optically detect the presence of medications. Other devices for sensing medications are equally well suited.

Microprocessor 74 compares the signals received from sensors 140 with the prescription information stored within code card 10. Compliance information indicating whether or not the patient has taken medications in accordance with the prescribed medication schedule is then written into code card 10 through transducer 76. In many instances severe complications can result from the patient's failure to take medications at the prescribed time. To alleviate this problem, control module 70 includes transmitter 142 which is interfaced with microprocessor 74. Under control of microprocessor 74, transmitter 142 will transmit (through antenna 28), an alarm signal to monitor 42 at the nursing station. Hospital or nursing home staff are alerted to the fact that a patient failed to take their medications. Appropriate action can then be implemented.

Yet another embodiment of medication dispenser 22 includes a printer 144, which is interfaced with microprocessor 74 and produces a printed record of all prescription information and/or patient compliance information stored within code card 10. Preferred embodiments of medication dispenser 22 also includes a reservoir 150 for holding water. A pump 152 is actuated by electrical or mechanical means (not shown) and forces water out faucet 154. Reservoir 150, pump 152, and faucet 154 are a convenient means of providing the water which a patient may need as an aid to taking medications.

C. HOME MEDICATION DISPENSER

A medication dispenser which is particularly well suited for use within the home of individual patients is illustrated in FIGS. 7-10. Home unit 160 embodies many of the same features already described with reference to the hospital and nursing home version of medication dispenser 22.

Home unit 160 includes a control module which is comprised of a front housing 162 and a rear housing 164. Front housing 162 is formed by front panel 240, top panel 242, side panels 244 and 246, and a bottom panel 248. Rear housing 164 is an elongated housing which extends rearwardly from a back side of front housing 162. Rear housing 164 is formed by top panel 250, bottom panel 252, and side panels 254. Rear housing 164 is enclosed by end panel 256. All electrical and electro-mechanical systems required to operate home unit 160 are contained within front housing 162 and rear housing 164. Power for home unit 160 is supplied by batteries 166 which are preferably mounted within front housing 164. Preferred embodiments of home unit 160 includes rechargeable batteries which are recharged from an adapter (not shown) powered by connection to a standard 120 volt AC outlet.

Electronic control for home unit 160 is provided by microprocessor 161. In preferred embodiments, microprocessor 161 is mounted within front housing 162. Like the hospital and nursing home version, microprocessor 161 of home unit 160 will include a real time clock, Input/Output ports, read only memory (ROM) and random access memory (RAM). Although the interconnections are not shown, microprocessor 151 is interfaced with all electrical and electro-mechanical systems within home unit 160.

As shown in FIG. 7, home unit 160 includes a clock display 168 which is preferably a digital LED or LCD display mounted to front panel 240 of front housing 164. Clock display 168 provides a digital indication of the correct time of day. As will be described later, clock display 168 is also used in programming home unit 160.

Home unit 160 preferably includes both audio and visual alarms. The audio alarm is provided by speaker 170 which is interfaced with microprocessor 161 and mounted to front panel 240. Volume control 172 is used to adjust the volume of the audio alarm. Speaker 170 will typically produce a beeping tone as an alarm. Visual alarms are provided by lights 174. Each light 174 is interfaced with microprocessor 161. Lights 174 are mounted on top panel 250 of rear housing 164 adjacent to compartments 176.

Like the hospital and nursing home unit, home unit 160 includes a plurality of individual compartments 176. Each compartment 176 is designed to be filled with all medications which are to be taken at a prescribed time. As best shown in FIG. 9, compartments 176 are detachable from rear housing 164. The embodiment shown include four rows of compartments, 180, 182, 184, and 186. Each of rows 180, 182, 184 and 186 includes seven compartments 176. Other combinations of compartments are equally well suited. Each compartment 176 includes a front wall 190, a bottom wall 192, a rear wall 194 and side walls 195. A top of each compartment is covered by door 196. Each door 196 is mounted to rear wall 194 by hinge 198. A spring 200 biases door 196 in a normally closed position, covering container 176, and retaining the medications therein.

Front wall 190 of each compartment 176 includes indent 202. As best shown in FIG. 9, each door 196 has an end portion 204 which extends beyond indent 202. By placing a finger within indent 202 and under front edge 204, the patient can easily open door 196 at the prescribed time and remove the medications therein.

Rows 180, 182, 184 and 186 of compartments 176 are attached to rear housing 164 by split ball fasteners 210. As shown in FIG. 9, each rear wall 194 of container 176 includes a plurality of split ball fasteners 210. These fasteners are aligned with matching holes 212 in side walls 254 of rear housing 164. Split balls 210 will compress when inserted into holes 212 and expand after entering an interior of rear housing 164. All containers 176 are rigidly attached to rear housing 164 in this manner.

Like the hospital and nursing home version, home unit 160 also includes means for making medications within individual compartments 176 available to the patient only at prescribed times. As best shown in FIGS. 9 and 10, each door 196 includes a rear edge 220 which extends beyond hinge 198. Mounted within rear housing 164 of the control module, and adjacent each compartment 176, is an electro-mechanical actuator 222. Each actuator 222 is interfaced with microprocessor 161. Actuators 222 each include a pin 224. In an unactuated state, pins 224 extend outward from actuators 222 and will be positioned below rear edge 220 of doors 196. Doors 196 are inhibited from opening and the patient will be unable to remove medications from the compartments 176. At the prescribed times, microprocessor 161 will actuate the proper actuator 222 and retract pin 224. At the same time microprocessor 161 will activate an audio alarm from speaker 170 and turn on the light 174 adjacent the compartment 176 from which medications are to be taken. The patient can then open door 196 and remove medications from that particular compartment 176. The patient will then depress alarm switch 230 and light switch 232 (shown in FIG. 7) to deactivate the audio and visual alarms. This procedure is repeated at all prescribed times programmed into home unit 160.

As best shown in FIG. 9, sensors 233 are mounted to side walls 254 of rear housing 164 adjacent to doors 196. Each sensor 233 is interfaced with microprocessor 161. When opened, the rear edge 220 of door 196 will actuate sensor 233. Sensors 233 thereby provide signals to microprocessor 161 indicating that the door was opened at the prescribed time and, presumably, that medications within the compartment 176 were taken. Microprocessor 161 stores this information within RAM.

Home unit 160 is operated by a pharmacist in the following manner. Each individual compartment 176 is first filled with medications in accordance with the times at which they are to be taken. Home unit 160 is then programmed to make the medications within the compartments available to the patient at the proper prescribed times. The pharmacist will program home unit 160 using mode switch 260, and set switch 262. These switches are located on front panel 240 as shown in FIG. 7. By depressing the mode switch the pharmacist will sequence through an entry routine program stored within ROM. This program stores prescribed times for each individual compartment 176. Display 168 will provide a visual indication of which compartment is being programmed. After operating mode switch 260 to arrive at the desired compartment, the pharmacist will use set switch 262 to program in the time of day at which that respective compartment 176 is to be accessible to the patient. Display 168 will provide a visual indication of the prescribed time being programmed into RAM for the particular compartment 176. This step is repeated for each compartment 176.

Mode switch 260 is also operated to sequence through a display routine program. The display program provides a visual representation on display 168 of the times at which medications were removed from the individual compartments 176. The pharmacist uses this information to monitor the patient's compliance with the prescribed medication schedule.

The embodiment shown in FIG. 7 can be programmed to provide medications to a patient once a day for 28 days. Alternatively, the device can be programmed to provide medications four times per day for a week. Any other combinations can also be used.

D. CONCLUSION

In summary, the present invention is a system, apparatus and method for distributing medications to a patient. Unlike conventional medication distribution devices, the present invention is programmed to distribute medications to a patient at prescribed times. All prescription information is stored within a portable memory device. This device is reliable and easy to use. The information is also stored in high density form. Tedious filing procedures and voluminous storage files are therefore eliminated.

When using the system of the present invention a pharmacist will fill individual compartments of a container with medications to be taken at prescribed times. The container will hold a supply of medications lasting the patient for a period of time from one day to one month. The memory device is then programmed accordingly. Hospital or nursing home staff transport the container and memory device to the patient and load them into a dispenser. The dispenser will then present the medications to the patient at the prescribed times. The patient removes the medications from the compartments an ingests them. A significant reduction in time and expense is achieved since hospital personnel are no longer required to regularly distribute medications throughout the day. Since all prescription information is stored within the memory device hospital personnel can easily access this information through a monitor. Similarly, this information can be transmitted by a modem to a remote receiving station over a standard communication line. Another important feature of the invention resides in comparator apparatus located within the medication dispenser. The dispenser checks whether or not the patient is taking medications as prescribed. This patient compliance information is stored within the memory device and can be reviewed by hospital or nursing home personnel. This information is very important in ensuring proper patient care.

Although the present invention has been described with reference to preferred embodiments, those skilled in the art will realize that changes may be made in form and detail without departing from the spirit and scope of the invention.

What is claimed is:

1. A modular system for distributing and dispensing medications, including:
    portable memory means for storing data representative of patient medication dispensing information and capable of use with other elements of the system including programming means, dispenser means and monitor means;
    programming means, including means for releasably receiving the portable memory means, for receiving medication dispensing information and for writing data representative of the medication dispensing information to the portable memory means;
    dispenser means for dispensing prescribed medications, the dispenser means including:
        memory receiving means for releasably receiving the portable memory means to which data representative of the medication dispensing information has been written through use of the programming means;
        read means for reading the data representative of the medication dispensing information from the portable memory means when the portable memory means is positioned in the memory receiving means;
        container means having a plurality of individual compartments for storing prescribed medications;
        control means coupled to the read means for providing control signals as a function of the data representative of the medication dispensing information;
        access means coupled to the control means and responsive to the control signals for making the prescribed medications within individual compartments of the container means accessible to a patient at prescribed times in accordance with the data representative of the medication dispensing information;
        sensor means for sensing patient compliance information representative of whether the prescribed medications were accessed by the patient when made accessible by the access means;
        write means coupled to the sensor means for writing data representative of the patient compliance information to the portable memory means when the portable memory means is positioned in the memory receiving means; and
    monitor means, including memory receiving means for releasably receiving the portable memory means, for providing a display of the medication dispensing information and the patient compliance information stored by the portable memory means; wherein the programming means, dispenser means and monitor means can be positioned at locations remote from each other.

2. The system of claim 1 and including transmitter means for transmitting over a communication line the data stored by the portable memory means.

3. The system of claim 1 wherein the dispenser means includes means for producing an output representing the medication dispensing information and the patient compliance information stored by the portable memory means.

4. The system of claim 1 wherein the dispenser means includes alarm means coupled to the control means and responsive to the control signals, for indicating the accessibility of prescribed medications at prescribed times.

5. The system of claim 1 wherein the medication dispensing information written to the portable memory means includes patient identification data.

6. The system of claim 5 wherein the medication dispensing information written to the portable memory means includes medication data.

7. The system of claim 6 wherein the medication dispensing information written to the portable memory means includes dosage data.

8. The system of claim 7 wherein the medication dispensing information written to the portable memory means includes time data.

9. The system of claim 1 wherein the sensor means of the dispenser means includes means for providing information representative of whether the prescribed medications were removed from the compartments of the container means when made accessible by the access means.

10. The system of claim 9 wherein the sensor means of the dispenser means includes means for detecting the presence of objects, including medications, in the compartments of the container means.

11. The system of claim 1 wherein the programming means includes a keyboard.

12. A medication dispensing device for use in conjunction with a modular medication dispensing system of the type also including a portable memory device for storing medication dispensing information and patient compliance information, a programmer for releasably receiving the memory device and for writing the medication dispensing information to the memory device, and a monitor for releasably receiving the memory device and for providing a display of medication dispensing information and patient compliance information stored by the memory device, the medication dispensing device including:

container means having a plurality of individual compartments, each of which is adapted to be filled with medications to be taken by a patient at a prescribed time;

memory receiving means for releasably receiving a portable memory device to which medication dispensing information, including prescribed times, has been written through use of the programmer;

read means for reading the medication dispensing information from the memory device;

control means coupled to the read means for providing control signals as a function of the medication dispensing information read from the memory device;

access means coupled to the control means and responsive to the control signals for making each individual compartment and the medications therein accessible to the patient at the prescribed time;

sensor means for sensing patient compliance information representative of whether the prescribed medications were accessed by the patient when made accessible by the access means; and write means coupled to the sensor means for writing the patient compliance information to the portable memory device so that the patient compliance information can be displayed by the monitor when the memory device is removed from the dispenser and received by the monitor.

13. The medication dispensing device of claim 12 wherein the container means is circular and wherein the individual compartments are circumferentially spaced about the container means.

14. The medication dispensing device of claim 13 wherein the access means for making each individual compartment and the medications therein accessible to the patient at the prescribed times include:

a cover positioned adjacent to the compartments of the container means and having an opening of a size through which medications in one compartment are accessible; and actuator means connected to receive control signals from the control means and for providing relative movement between the cover and the container means to align a compartment and the opening in the cover at the prescribed time.

15. The medication dispensing device of claim 14 and including lock means for locking the cover adjacent to the compartments of the container means.

16. The medication dispensing device of claim 14 wherein the actuator means includes a motor having a drive shaft.

17. The medication dispensing device of claim 16 wherein the motor includes gear means attached to the drive shaft for engaging and rotating the container means.

18. The medication dispensing device of claim 14 and including door means for covering the opening in the cover.

19. The medication dispensing device of claim 18 wherein the door means includes safety latch means for prohibiting access to the medications by unauthorized persons.

20. The medication dispensing device of claim 12 wherein the sensor means for sensing patient compliance detects presence of objects including medications within the compartments of the container means.

21. The medication dispensing device of claim 12 and including alarm means for indicating the accessibility of the medications at the prescribed times.

22. The medication dispensing device of claim 12 wherein the container means is detachable from the access means for making each individual compartment and the medications therein accessible to the patient.

23. The medication dispensing device of claim 12 and including liner means for lining the compartments of the container means.

24. The medication dispensing device of claim 12 and further including printer means coupled to the read means for producing an output representing the medication dispensing information and the patient compliance information stored by the memory device.

25. The medication dispensing device of claim 12 and further including keyboard means coupled to the write means for entering medication dispensing information into the memory device.

26. The medication dispensing device of claim 12 and including means for dispensing water.

27. A medication dispensing device for use in conjunction with a modular medication dispensing system of the type also including a portable memory device for storing medication dispensing information and a programmer for releasably receiving the memory device and for writing medication dispensing information to the memory device, the medication dispensing device including:

portable container means having a plurality of individual compartments to be filled with medications for a patient in accordance with medication dispensing information, wherein each compartment is to contain medications which are to be taken at a prescribed time; and a control module cooperable with the container means and including:

memory receiving means for releasably receiving the memory device to which medication dispensing information has been written by the programmer;

container receiving means for releasably receiving the container means so as to permit the container means to be filled with medications at a location remote from the control module;

read means positioned with respect to the memory receiving means for reading the medication dispensing information from the memory device when the memory device is positioned in the memory receiving means;

control means connected to the read means for providing control signals in accordance with the medication dispensing information read from the memory device; and access means responsive to the control means for making individual compartments of the container means and the medications therein accessible to a patient at the prescribed time in accordance with the medication dispensing information.

28. The medication dispensing device of claim 27 wherein the container means is circular and wherein the individual compartments are circumferentially spaced about the container.

29. The medication dispensing device of claim 28 wherein the access means of the control module includes:

a cover positioned adjacent to the compartments of the container means and having an opening of a size through which medications in only one compartment are accessible; and actuator means responsive to the control means for providing relative rotation between the cover and the container means, the actuator means aligning the opening in the cover with the compartment of the container at the prescribed time.

30. The medication dispensing device of claim 29 wherein the control module includes:

sensor means coupled to the control means for sensing patient compliance information representative of whether medications were accessed by the patient when made accessible in accordance with the prescription information, and for providing signals in response thereto; and write means coupled to the control means for writing the patient compliance information to the memory device when the memory device is positioned in the memory receiving means of the control module.

31. The medication dispensing device of claim 30 wherein the sensor means for sensing patient compliance includes means for detecting presence of objects including medications within the compartments of the container means.

32. The medication dispensing device of claim 29 wherein the control module includes lock means for locking the cover adjacent to the compartments of the container means.

33. The medication dispensing device of claim 29 wherein the actuator means includes a motor having a drive shaft.

34. The medication dispensing device of claim 33 wherein the motor includes gear means mounted to the drive shaft for engaging and rotating the container means.

35. The medication dispensing device of claim 29 and including door means for covering the opening in the cover.

36. The medication dispensing device of claim 35 and including safety latch means for prohibiting unauthorized persons from opening the door means and accessing the medications.

37. The medication dispensing device of claim 27 wherein the control module includes alarm means for indicating the accessibility of medications at the prescribed times.

38. The medication dispensing device of claim 27 and including detachable liners which are positioned within the compartments of the container means.

39. The medication dispensing device of claim 27 and including keyboard means connected to the control means for entering medication dispensing information, and write means coupled to the control means and positioned with respect to the memory receiving means for writing the medication dispensing information entered by the keyboard means to the memory device.

40. The medication dispensing device of claim 27 and including means for dispensing water.

41. A modular medication dispensing and distribution system, including:

portable memory means for storing data representative of patient medication dispensing information and capable of use with other elements of the system including programming means and dispenser means;

programming means, including means for releasably receiving the portable memory means, for receiving medication dispensing information and for writing data representative of the medication dispensing information to the portable memory means; and dispenser means for dispensing prescribed medications, the dispenser means including:

portable container means having a plurality of individual compartments to be filled with medications in accordance with the medication dispensing information; and a control module cooperable with the container means and including:

memory receiving means for releasably receiving the portable memory means to which data representative of medication dispensing information was written by the programming means;

container receiving means for releasably receiving the portable container means so as to permit the container means to be filled with medications at a location remote from the control module;

read means positioned with respect to the memory receiving means for reading data representative of the medication dispensing information from the memory means when the memory means is positioned in the memory receiving means;

control means coupled to the read means for providing control signals in accordance with the data representative of the medication dispensing information read from the memory means; and access means coupled to the control means and responsive to the control signals for making medications within individual compartments of the portable container means accessible to a patient in accordance with the medication dispensing information.

42. The system of claim 41 wherein the control module of the dispenser means further includes:

sensor means for sensing patient compliance information representative of whether the prescribed medications were accessed by the patient when made accessible by the access means; and write means coupled to the sensor means for writing data representative of the patient compliance information to the portable memory means when the portable memory means is positioned in the memory receiving means of the control module.

43. The system of claim 41 wherein the sensor means of the dispenser means includes means for providing information representative of whether the prescribed medications were removed from the compartments of the container means when made accessible by the access means.

44. The system of claim 43 wherein the sensor means of the dispenser means includes means for detecting presence of objects, including medications, in the compartments of the container means.

45. The system of claim 41 wherein the programming means includes a keyboard.

* * * * *